US009689843B2

(12) United States Patent
Kinoshita et al.

(10) Patent No.: US 9,689,843 B2
(45) Date of Patent: Jun. 27, 2017

(54) FLUID STATE IDENTIFICATION DEVICE

(71) Applicant: SUN-A Corporation, Hiroshima (JP)

(72) Inventors: Yasuyuki Kinoshita, Hiroshima (JP); Fumikazu Nakayama, Hiroshima (JP); Shinji Kiyomihara, Hiroshima (JP); Yasuhiko Shimada, Hiroshima (JP); Shinkichi Ninomiya, Hiroshima (JP)

(73) Assignee: SUN-A CORPORATION, Hiroshima (JP)

( * ) Notice: Subject to any disclaimer, the term of this patent is extended or adjusted under 35 U.S.C. 154(b) by 132 days.

(21) Appl. No.: 14/434,265

(22) PCT Filed: Oct. 4, 2013

(86) PCT No.: PCT/JP2013/077039
§ 371 (c)(1),
(2) Date: Apr. 8, 2015

(87) PCT Pub. No.: WO2014/057872
PCT Pub. Date: Apr. 17, 2014

(65) Prior Publication Data
US 2015/0260687 A1  Sep. 17, 2015

(30) Foreign Application Priority Data

Oct. 9, 2012 (JP) ................................ 2012-224435

(51) Int. Cl.
*G01N 29/032* (2006.01)
*G01N 29/02* (2006.01)
(Continued)

(52) U.S. Cl.
CPC ........... *G01N 29/02* (2013.01); *F01N 3/2066* (2013.01); *F01N 11/00* (2013.01); *G01N 25/18* (2013.01);
(Continued)

(58) Field of Classification Search
CPC ............................................ G01N 2291/02836
(Continued)

(56) References Cited

U.S. PATENT DOCUMENTS 7,302,830 B2 * 12/2007 Kolosov .................. G01N 9/32
73/53.01
7,703,276 B2 * 4/2010 Ueno ...................... F01N 3/208
239/132
(Continued)

FOREIGN PATENT DOCUMENTS

EP         1669742    *  9/2004  ............. G01N 27/18
JP         2005-084025    3/2005
(Continued)

OTHER PUBLICATIONS

Yasuyuki, Kinoshita, 'Fluid State Identification Device', PCT/JP2013/077039 Written Opinion of the International Searching Authority, Oct. 4, 2013, 4 pages.*
(Continued)

Primary Examiner — Clayton E LaBalle
Assistant Examiner — Kevin Butler
(74) Attorney, Agent, or Firm — Young & Thompson

(57) ABSTRACT

Provided is a fluid state identification device including a fluid state identification unit having a sensor part and a support part, and a cover surrounding the fluid state identification unit. The support part has a front surface part and a rear surface part which are located opposite to each other. The sensor part is located on the front surface part side. The cover has a lower opening and an upper opening. Inside the cover, a first fluid flow route running through a front area adjacent to the support front surface part and a second fluid flow route running through a rear area adjacent to the support rear surface part are formed and located so as to make the fluidity of the fluid in the second fluid flow route higher than the fluidity of the fluid in the first fluid flow route.

18 Claims, 23 Drawing Sheets

(51) Int. Cl.
*G01N 25/18* (2006.01)
*G01N 29/22* (2006.01)
*G01N 27/18* (2006.01)
*F01N 11/00* (2006.01)
*G01N 29/32* (2006.01)
*F01N 3/20* (2006.01)
*G01F 1/74* (2006.01)

(52) U.S. Cl.
CPC ........... *G01N 27/18* (2013.01); *G01N 29/222* (2013.01); *G01N 29/32* (2013.01); *F01N 2550/05* (2013.01); *F01N 2610/02* (2013.01); *F01N 2610/148* (2013.01); *F01N 2900/1818* (2013.01); *G01F 1/74* (2013.01); *G01N 29/032* (2013.01); *G01N 2291/011* (2013.01); *G01N 2291/022* (2013.01); *G01N 2291/0228* (2013.01); *G01N 2291/02416* (2013.01); *G01N 2291/02425* (2013.01); *G01N 2291/02809* (2013.01); *G01N 2291/02836* (2013.01); *Y02T 10/24* (2013.01); *Y02T 10/47* (2013.01)

(58) Field of Classification Search
USPC ........................................................ 73/61.79
See application file for complete search history.

(56) References Cited

U.S. PATENT DOCUMENTS

| | | | | |
|---|---|---|---|---|
| 2003/0135072 | A1* | 7/2003 | Scholten | C07C 273/04 564/67 |
| 2005/0229677 | A1* | 10/2005 | Tuller | B01D 53/9409 73/24.01 |
| 2008/0038153 | A1* | 2/2008 | Yamamoto | G01F 23/268 422/82.12 |
| 2008/0247912 | A1* | 10/2008 | Izutani | F01N 11/00 422/82.12 |
| 2008/0257912 | A1* | 10/2008 | Bach | F04B 13/00 222/333 |
| 2014/0041442 | A1* | 2/2014 | Heinrich | G01F 23/296 73/61.79 |
| 2014/0080115 | A1* | 3/2014 | Reed | G01N 15/0618 435/3 |
| 2014/0227137 | A1* | 8/2014 | Iida | B01D 53/9418 422/111 |
| 2015/0308952 | A1* | 10/2015 | Johnson | G01N 21/59 356/436 |
| 2016/0123929 | A1* | 5/2016 | Op De Beeck | G01N 29/02 73/632 |
| 2016/0146776 | A1* | 5/2016 | Akiyoshi | F01N 3/206 73/64.53 |

FOREIGN PATENT DOCUMENTS

| | | | | |
|---|---|---|---|---|
| JP | 2005084025 | * | 3/2005 | ............... F01N 3/00 |
| JP | 2007-263950 | | 10/2007 | |
| JP | 2008-064741 | | 3/2008 | |
| JP | 2011-218670 | | 11/2011 | |
| JP | 2011-242227 | | 12/2011 | |

OTHER PUBLICATIONS

Yasuyuki, Kinoshita, 'Fluid State Identification Device', PCT/JP2013/077039 International Search Report (ISR), Nov. 5, 2013, 1 page.*
International Search Report, PCT/JP2013/077039, Nov. 19, 2013.

* cited by examiner

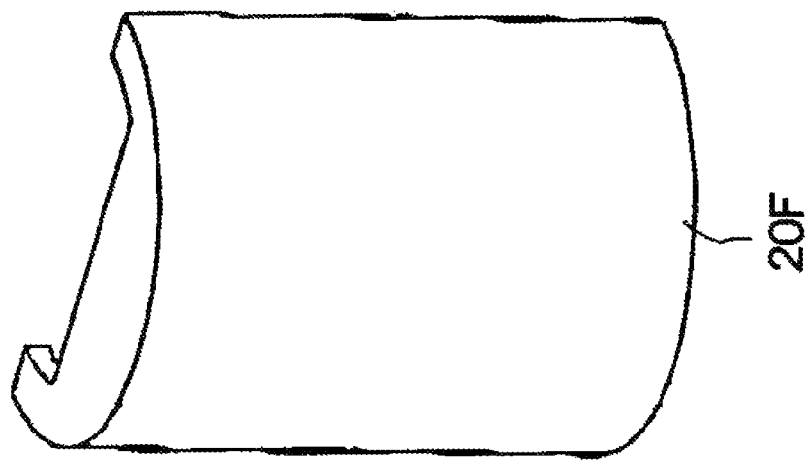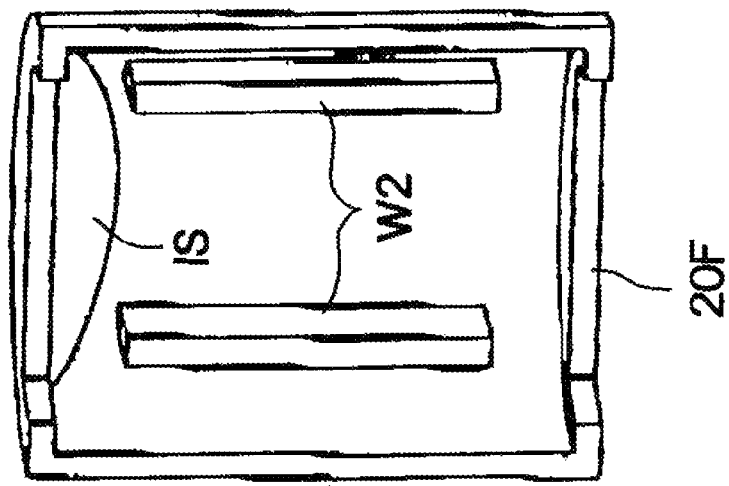

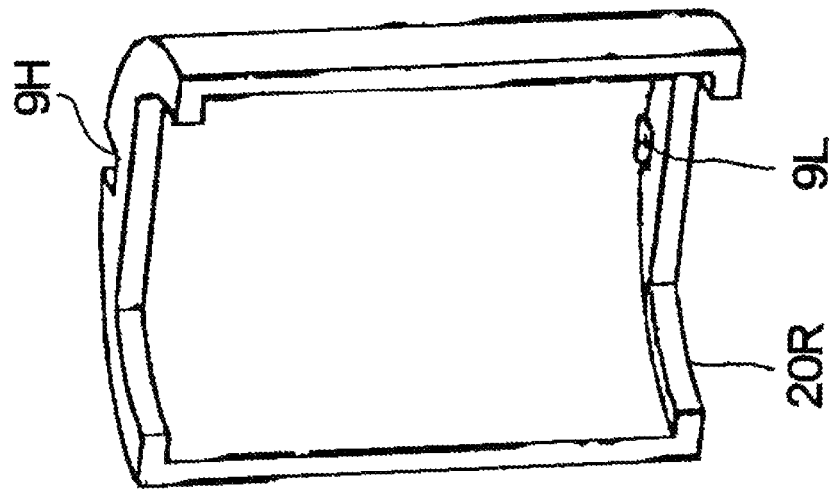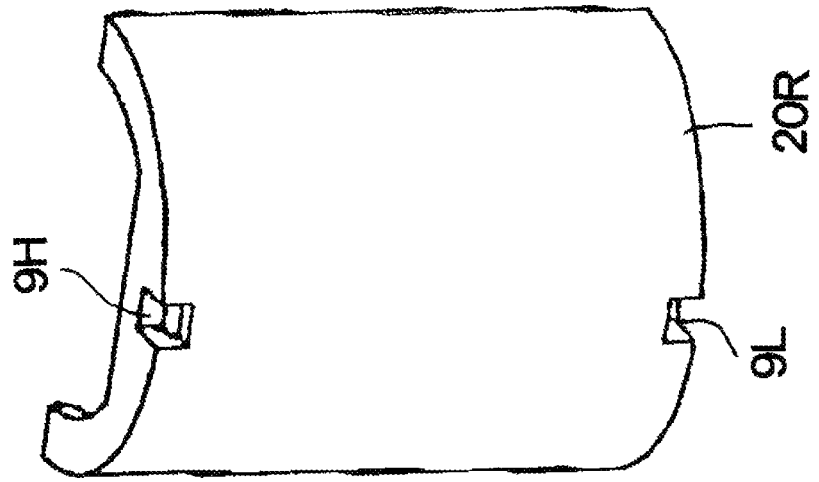

FLUID STATE IDENTIFICATION DEVICE

TECHNICAL FIELD

The present invention relates to fluid state identification devices which identify the state of a fluid such as a liquid or a solid-liquid mixture containing solid particles in a liquid, and more particularly to a liquid identification device which includes a fluid state identification unit having a fluid state identification sensor part and a cover surrounding the fluid state identification unit.

BACKGROUND ART

A fossil fuel such as gasoline or light oil is burned in the internal combustion engine of a vehicle. The exhaust gas generated by burning of the fossil fuel contains environmental pollutants such as unburned carbon monoxide (CO), carbon hydride (HC), sulfur oxide (SOx), nitrogen oxide (NOx) and so forth, as well as water and carbon dioxide. In the recent years, various countermeasures to purify vehicle exhaust gas have been adopted particularly in order to protect the environment and prevent pollution of living environments.

One such countermeasure is the use of an exhaust gas purifying catalyst device. In this countermeasure, a three-way catalyst for purifying exhaust gas is placed midway in the exhaust system, where CO, HC, NOx and the like are decomposed by oxidation-reduction reaction to make them harmless. In order to ensure continuous decomposition of NOx in the catalyst device, a urea aqueous solution is sprayed over the catalyst from immediately upstream of the catalyst device in the exhaust system.

The urea aqueous solution is contained in a urea aqueous solution tank mounted in a vehicle and its concentration may change over time and in the tank, uneven concentration distribution may occur locally. Since the urea aqueous solution being supplied from the tank through a supply pipe to a spray nozzle by a pump is generally taken through the tank outlet near the tank bottom, for enhancement of the efficiency of the catalyst device it is important that the urea aqueous solution in this area has prescribed urea concentration.

It may actually happen that a liquid other than a urea aqueous solution is mistakenly contained in the urea aqueous solution tank. In that case, it is necessary to detect quickly that the liquid is not a urea aqueous solution with prescribed urea concentration and give a warning, in order for the catalyst device to fulfill its function.

For this reason, a fluid state identification device is used to determine whether or not the aqueous solution is a urea aqueous solution whereof urea concentration is within a prescribed range. An example of this type of fluid state identification device is described in JPA 2007-263950 and some such devices have an identification sensor part including a thermal sensor, such as particularly an indirectly-heated sensor (indirectly-heated liquid type detector).

JPA 2007-263950 points out that deterioration in the identification performance of a liquid identification device is caused by the presence of air bubbles in the measured liquid, and describes that the surface of the identification sensor is covered by a hydrophilic film so as to prevent adhesion of air bubbles and improve the identification performance. JPA 2007-263950 also points out that deterioration in the identification performance of the liquid identification device is caused by forced flow of the measured liquid, and describes that a flow control plate surrounding a thermal sensor is provided in the identification sensor part to improve the identification performance.

JPA 2005-84025 points out that deterioration in the identification performance of a liquid identification device with an identification sensor part including a thermal sensor is caused by forced flow of the measured liquid due to vibration of the tank, etc. and describes that the identification sensor part is surrounded by a covering body and a hole for circulation is made in the covering body so as to improve the identification performance.

JPA 2011-218670 describes that an identification sensor part including a thermal sensor is formed by molding and it is covered by a covering body and a hole through which a liquid passes is made in the covering body.

JPA 2011-242227 describes that a drip tube is located opposite to a sensing part in order to avoid the influence of foam diffusion due to dripping of a urea aqueous solution.

CITATION LIST

Patent Literature

PTL 1: JPA 2007-263950
PTL 2: JPA 2005-84025
PTL 3: JPA 2011-218670
PTL 4: JPA 2011-242227

SUMMARY OF INVENTION

Technical Problem

However, the techniques disclosed in JPA 2007-263950, JPA 2005-84025, JPA 2011-218670 have points to be improved by suppressing both the unfavorable influence of bubbles in a measured fluid such as a measured liquid toward identification performance of a fluid state identification device such as a liquid identification device and the unfavorable influence of forced flow of a measured fluid such as a measured liquid to improve identification performance besides reducing the size of the device.

This kind of technical problem does not necessarily exist only in a liquid identification device with a fluid state identification sensor part including a thermal sensor because it is mainly caused by bubbles or forced flow in the area (place) of the measured fluid, where sensing by the sensor is performed. For example, JPA 2011-242227 points out that there is a similar technical problem in a fluid state identification device which performs sensing using a quality sensor in a prescribed area (place) of the measured liquid.

An objective of the present invention is to solve the above technical problems and particularly in a fluid state identification device, to reduce the unfavorable influence of bubbles in the measured fluid and forced flow of the measured fluid in order to improve the identification performance and also to enable downsizing the device easily.

Solution to Problem

According to the present invention, in order to achieve the above object, a fluid state identification device which includes a fluid state identification unit having a sensor part and a support part for supporting the sensor part and a cover surrounding the fluid state identification unit is provided. In the fluid state identification unit, the support part has a front surface part and a rear surface part which are located opposite to each other and the sensor part is located on the front surface part side. In the cover, a lower opening for communicating a lower part of the area between the cover and the fluid state identification unit with the outside and an upper opening for communicating an upper part of the area between the cover and the fluid state identification unit with the outside are formed. Inside the cover, a first fluid flow route running through a front area adjacent to the front surface part of the support part from the lower opening to the upper opening and a second fluid flow route running through a rear area adjacent to the rear surface part of the support part from the lower opening to the upper opening are formed. The lower opening and the upper opening are located so that fluid fluidity in the second fluid flow route is higher than fluid fluidity in the first fluid flow route.

According to an aspect of the present invention, the lower opening and the upper opening are located so that the distance to the rear area is smaller than the distance to the front area.

According to an aspect of the present invention, the lower opening and the upper opening are located so that the minimum sectional area of the second fluid flow route is larger than the minimum sectional area of the first fluid flow route.

According to an aspect of the present invention, a vertical passage adjacent to the sensor part is formed in the front area; and the vertical passage is surrounded by a left side wall located left of the sensor part, a right side wall located right of the sensor part, the front surface part of the support part and the cover, and its upper part and lower part are open.

According to an aspect of the present invention, the left side wall and the right side wall are each comprised of a first side wall member protruding from the front surface part of the support part and/or a second side wall member protruding from the inner surface of the cover.

According to an aspect of the present invention, a porous filter is located in a lower part of the vertical passage.

According to an aspect of the present invention, an opening having an area smaller than the area of an upper opening of the vertical passage is formed in a lower part of the vertical passage.

According to an aspect of the present invention, the top inner surface of the cover is an inclined surface.

Advantageous Effects of Invention

According to the fluid state identification device in the present invention, bubbles hardly flow into the front area where the fluid state is detected, particularly an area adjacent to the sensor part, and furthermore, forced flow of the measured fluid is unlikely to influence the front area, particularly the area adjacent to the sensor part, so that an unfavorable influence of bubbles in the measured fluid and forced flow of the measured fluid is reduced and the identification performance is improved; and this function can be obtained by a specific cover surrounding the fluid identification unit, so that the device can be easily downsized.

BRIEF DESCRIPTION OF DRAWINGS

FIGS. 7A and 7B are perspective views of the front cover part of the fluid state identification device shown in FIG. 1.

FIGS. 8A and 8B are perspective views of the rear cover part of the fluid state identification device shown in FIG. 1.

DESCRIPTION OF EMBODIMENTS

Next, embodiments of the present invention will be described referring to drawings.

Figure 1:
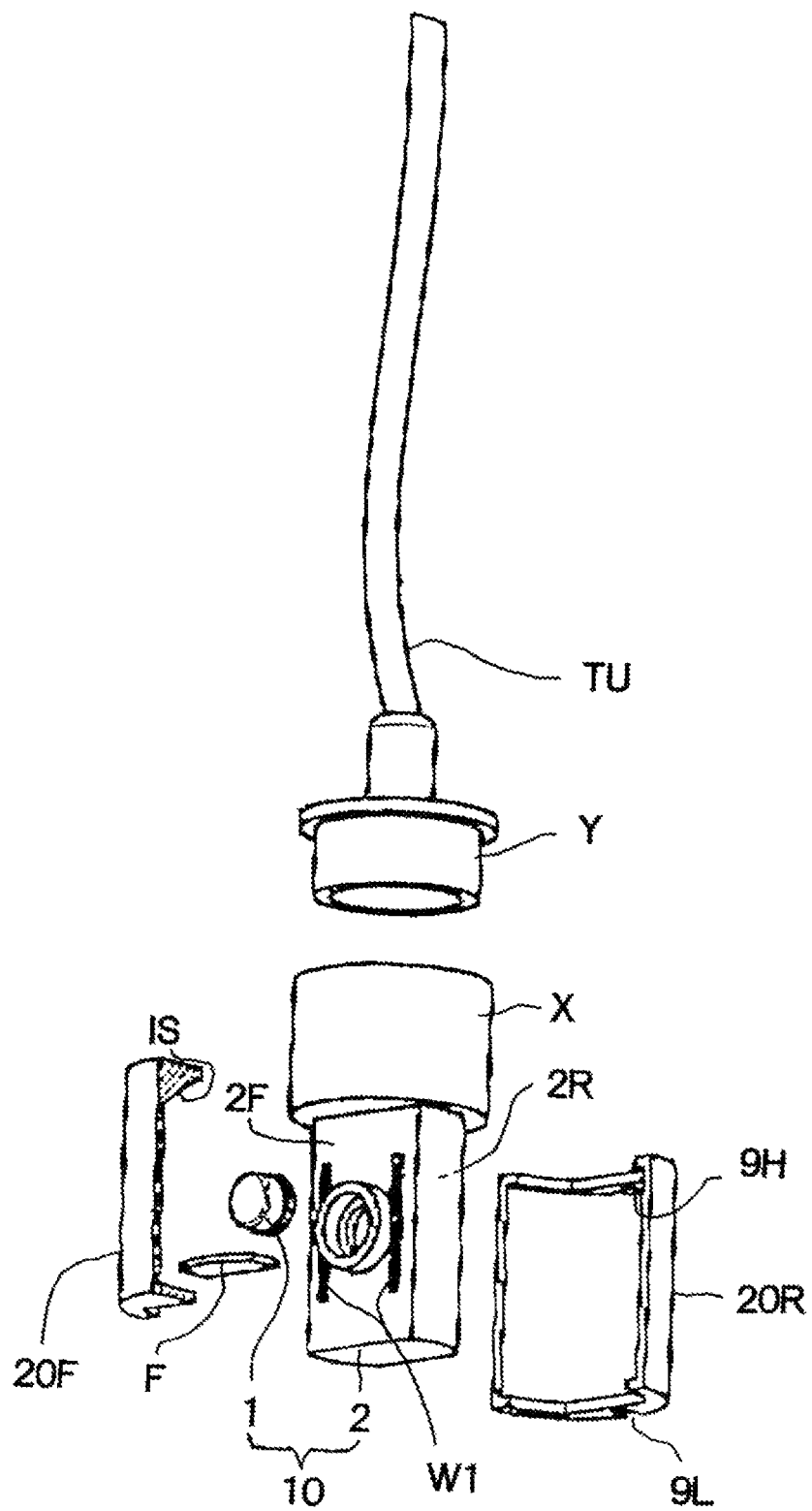
FIG. 1 is an exploded perspective view showing an embodiment of a fluid state identification device according to the present invention.
Figure 2:
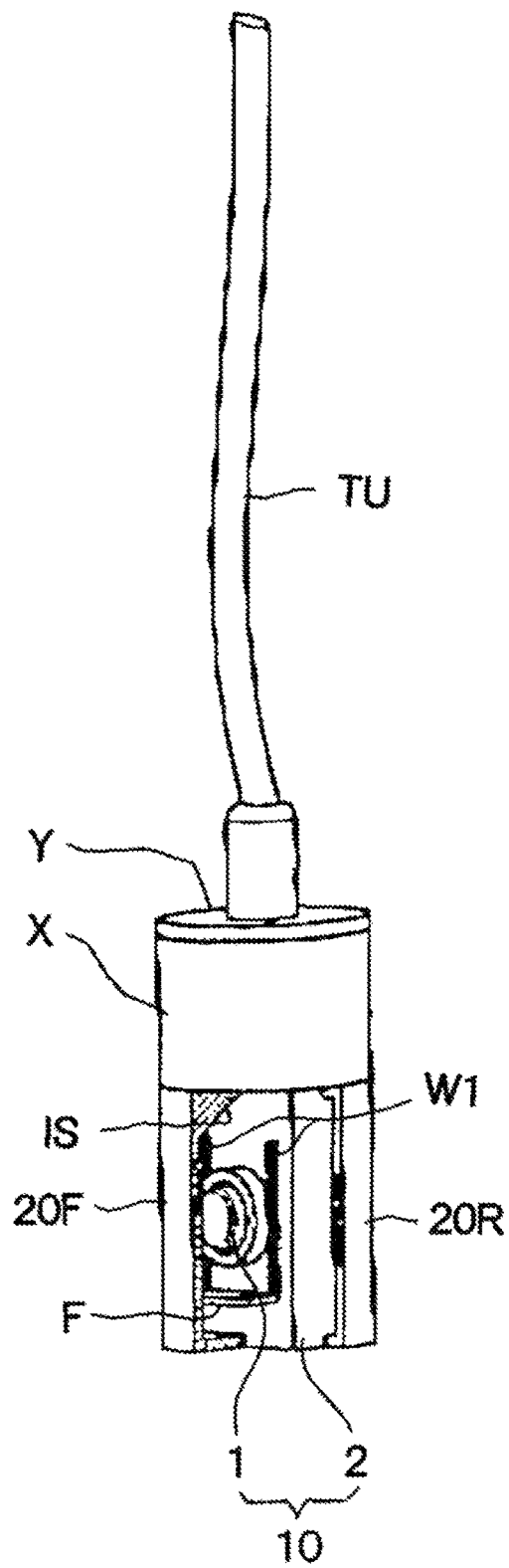
FIG. 2 is a partially cutaway perspective view of the fluid state identification device shown in FIG. 1.
Figure 3:
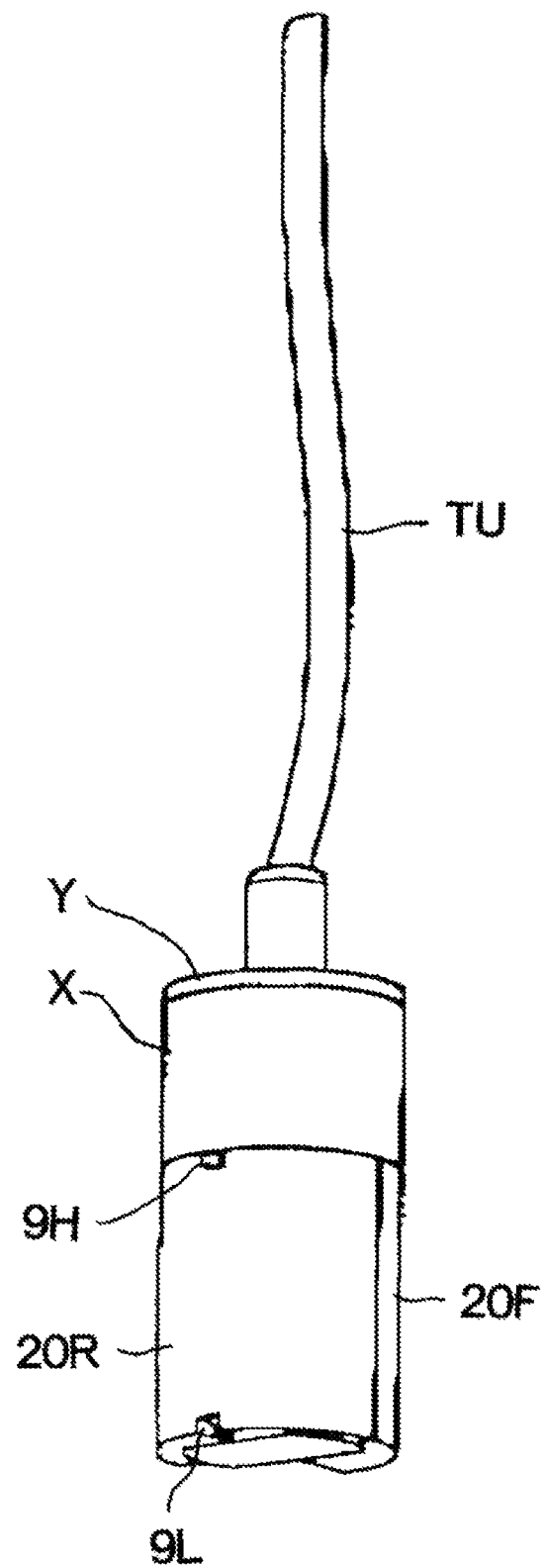
FIG. 3 is a perspective view of the fluid state identification device shown in FIG. 1.
Figure 4:
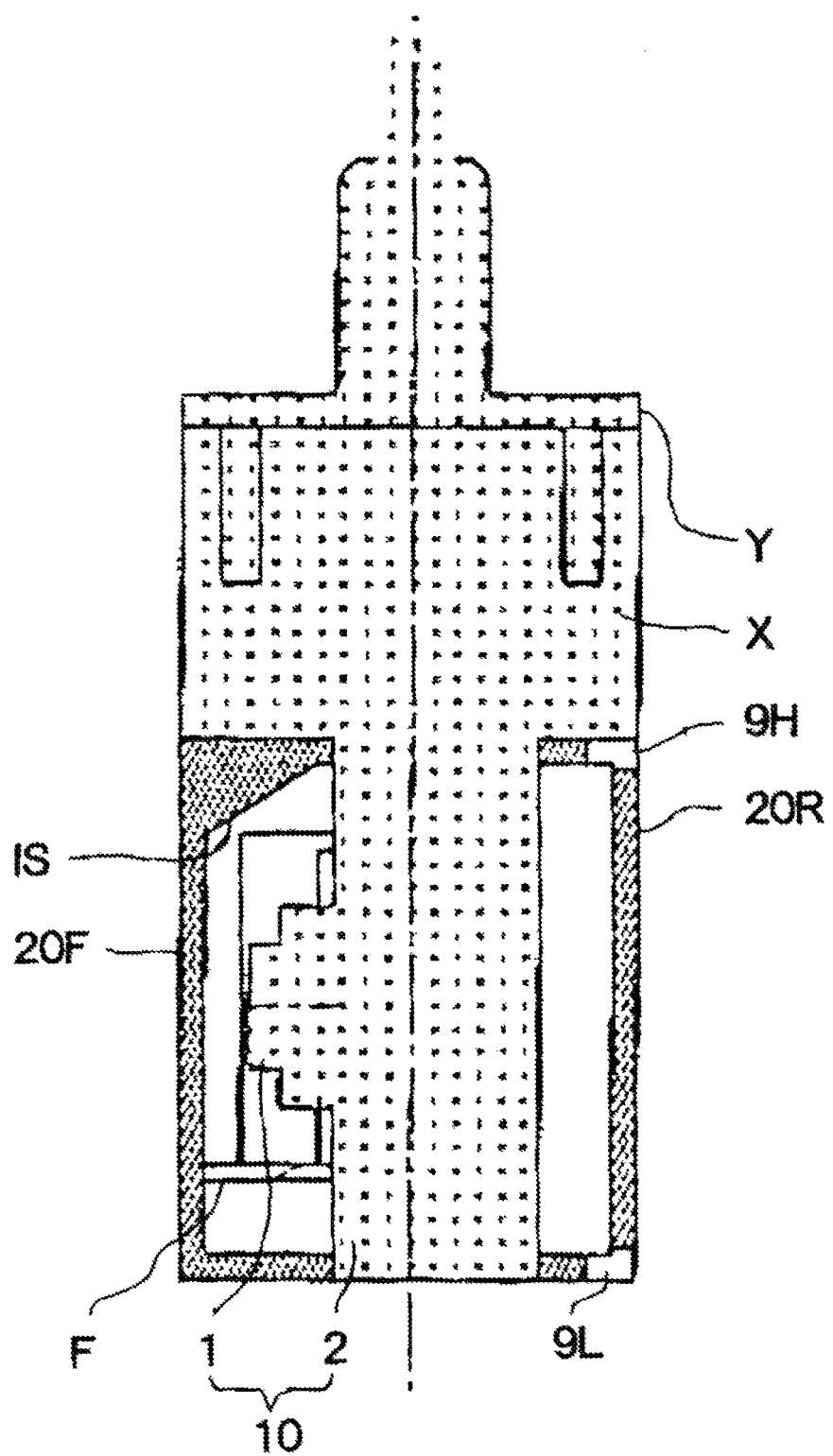
FIG. 4 is a schematic longitudinal sectional view of the fluid state identification device shown in FIG. 1.
Figure 5:
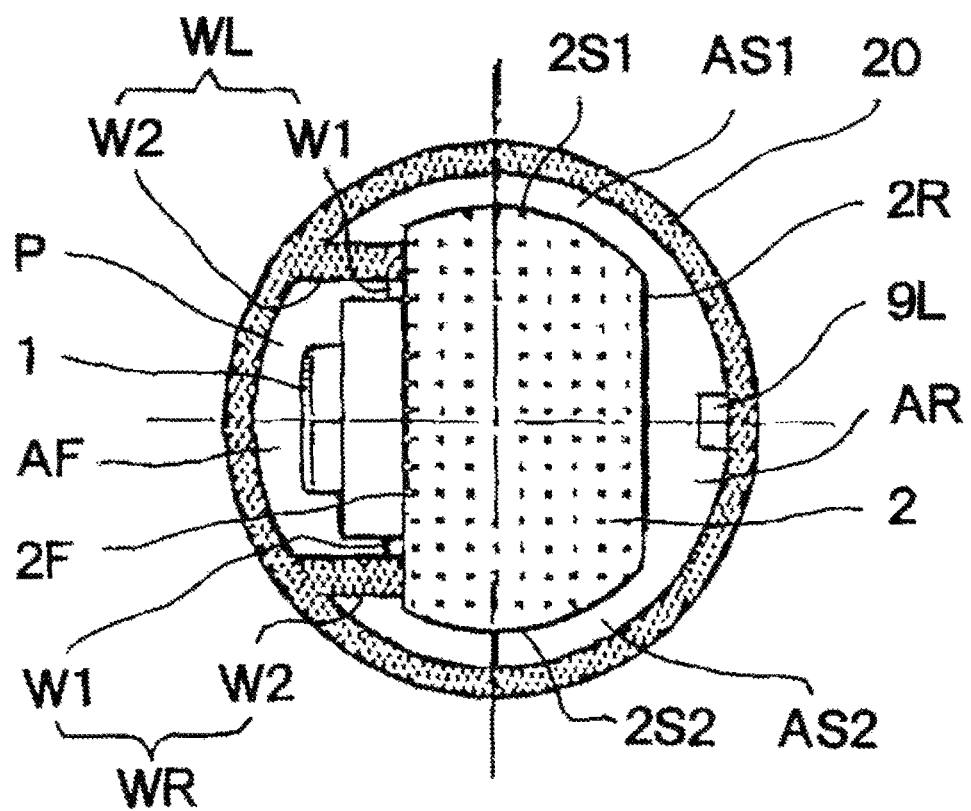
FIG. 5 is a schematic transverse sectional view of the fluid state identification device shown in FIG. 1.
Figure 6:
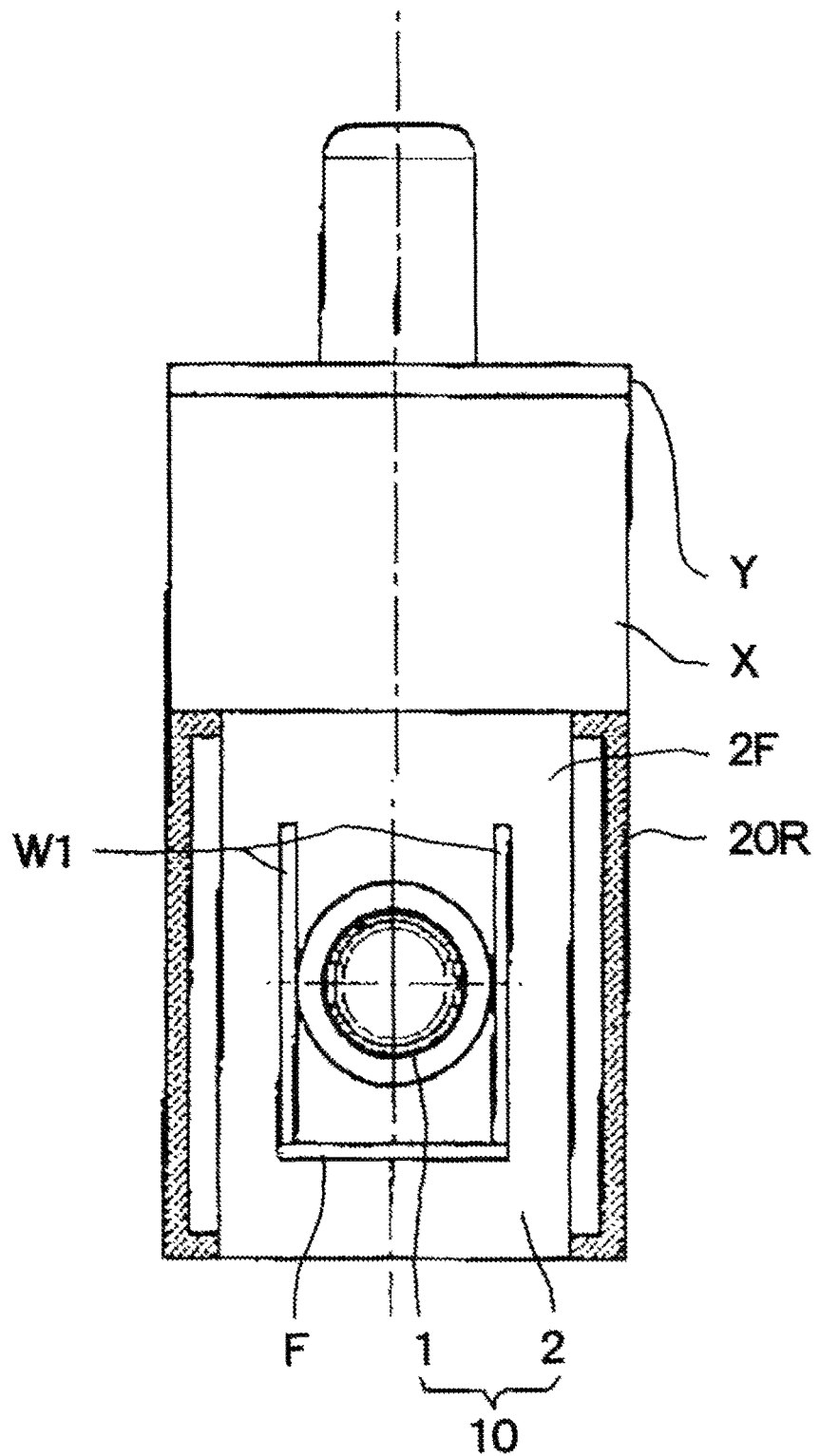
FIG. 6 is a partially cutaway front view of the fluid state identification device shown in FIG. 1.
Figure 9:
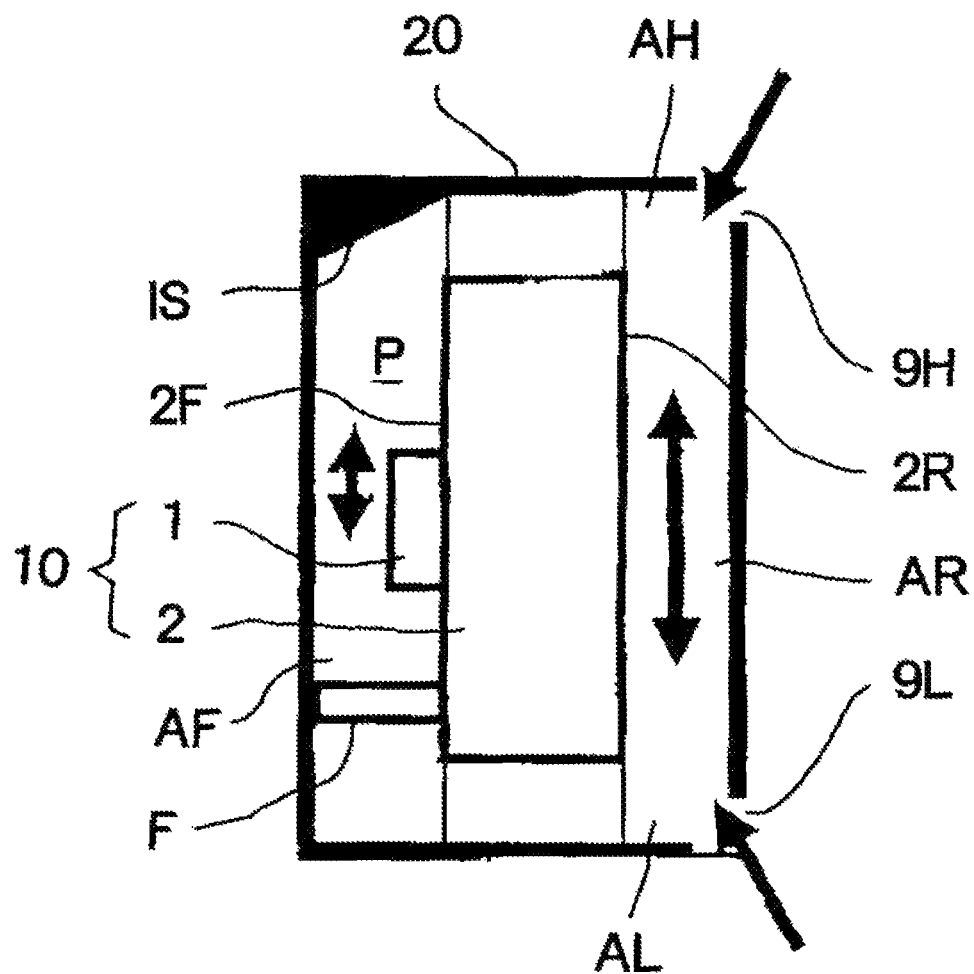
FIG. 9 is a schematic view for explaining the function of the fluid state identification device shown in FIG. 1.

FIG. 1 is a partially cutaway exploded perspective view showing an embodiment of a fluid state identification device according to the present invention; FIG. 2 is a partially cutaway perspective view of the fluid state identification device shown in FIG. 1; FIG. 3 is a perspective view of the fluid state identification device shown in FIG. 1; FIG. 4 is a schematic longitudinal sectional view of the fluid state identification device shown in FIG. 1; FIG. 5 is a schematic transverse sectional view of the fluid state identification device shown in FIG. 1; and FIG. 6 is a partially cutaway front view of the fluid state identification device shown in FIG. 1. FIGS. 7A and 7B are perspective views of the front cover part of the fluid state identification device shown in FIG. 1 and FIGS. 8A and 8B are perspective views of the rear cover part of the fluid state identification device shown in FIG. 1. FIGS. 9 to 13 are all schematic views for explaining the function of the fluid state identification device shown in FIG. 1, in which FIGS. 9, 10, and 12 correspond to longitudinal cross sections along the front-back direction, FIG. 11 corresponds to a longitudinal cross section along the left-right direction perpendicular to the front-back direction, and FIG. 13 corresponds to a transverse cross section along a horizontal plane.

In the present invention, words indicating directions such as "front", "back (rear)", "left", "right", "upper" and "lower" are defined on the assumption that the fluid state identification device is in use or the identification function is active. Therefore, these direction-related words are used here for explanatory convenience and, for example, in the stage of manufacture or distribution, it is obvious that the elements do not always have directionality as indicated by these words.

The fluid state identification device in this embodiment includes a fluid identification unit 10 having a sensor part 1 and a support part 2 for supporting the sensor part 1, and a cover 20 for surrounding the fluid identification unit 10. The cover 20 has a roughly cylindrical form in which a front cover part 20F and a rear cover part 20R are detachably attached to each other.

As illustrated in FIGS. 1 and 2, the fluid state identification device has a housing main part X with an opening at the top and a housing cover part Y fitted to the housing main part X liquid-tightly in a way to cover the top opening. The lower half of the housing main part X constitutes the support part 2 of the fluid identification unit 10. The support part 2 has a front surface part 2F and a rear surface part 2R which are located opposite to each other.

The sensor part 1 is located on the front surface part 2F of the support part 2 and fitted to an opening made in the front surface part 2F liquid-tightly.

On the other hand, a circuit board (not shown) is located inside the housing main part X and the sensor part 1 is connected to the circuit board.

The sensor part 1 is an identification sensor part which measures the characteristic value (for example, urea concentration) of a fluid such as a liquid in the urea aqueous solution tank and the sensor is, for example, an identification sensor module similar to the one described above in JPA 2007-263950.

The circuit board is further provided with several functional components for fluid state identification. Among these functional components are, for example, a digital circuit element such as a semiconductor integrated circuit element incorporating an arithmetic processing circuit and a memory, and an analog circuit element such as a transformer or capacitor. External connection wires are connected to the electric circuit of the circuit board and are passed through the housing cover part Y and inserted into a waterproof tube TU having a function to support the housing and the external connection wires extend outwards.

As illustrated in FIGS. 9 to 13, a front area AF adjacent to the front surface part 2F of the support part and a rear area AR adjacent to the rear surface part 2R of the support part are formed inside the cover 20 between the cover 20 and the fluid state identification unit 10 including the sensor part 1 and the support part 2. Also, a left area AS1 adjacent to the left side surface 2S1 of the support part 2 and a right area AS2 adjacent to the right side surface 2S2 of the support part 2 are formed between the cover 20 and the fluid state identification unit 10.

In the rear cover part 20R, a lower opening 9L for communicating a lower part AL, which is the area between the cover 20 and the fluid state identification unit 10, with the outside and an upper opening 9H for communicating an upper part AH, which is the area between the cover 20 and the fluid state identification unit 10, with the outside are formed.

Consequently, a first fluid flow route running through the front area AF adjacent to the front surface part of the support part from the lower opening 9L to the upper opening 9H and a second fluid flow route running through the rear area AR adjacent to the rear surface part of the support part from the lower opening 9L to the upper opening 9H are formed.

Here, the lower opening 9L and the upper opening 9H are located so that the fluid fluidity in the second fluid flow route is higher than the fluid fluidity in the first fluid flow route. Specifically, in this embodiment, the lower opening 9L and the upper opening 9H are located as the distance to the rear area AR become smaller than the distance to the front area AF. Thus, the fluidity inside the cover 20 of the fluid going in and out of the cover 20 through the lower opening 9L and upper opening 9H become higher in the second fluid flow route running through the rear area AR than in the first fluid flow route running through the front area AF as schematically indicated by both the arrows in FIG. 9.

In addition, a part of the top inner surface of the front cover part 20F which is located above the front area AF is an inclined surface IS. In this embodiment, the inclined surface IS is formed above the sensor part 1 in a form of receding upward in the leftward direction (see FIG. 11) and rightward direction (see FIG. 11) and/or the backward direction (see FIGS. 9, 10, and 12).

Furthermore, a vertical passage P adjacent to the sensor part 1 is formed in the front area AF. The vertical passage P is surrounded by a left side wall WL located left of the sensor part 1, a right side wall WR located right of the sensor part 1, the front surface part 2F of the support part and the front cover part 20F, and its upper part (upper end) and lower part (lower end) are open. The left side wall WL and right side wall WR are each comprised of a first side wall member W1 protruding from the front surface part 2F of the support part and a second side wall member W2 protruding from the inner surface of the front cover part 20F.

Alternatively, the left side wall WL and right side wall WR may be each comprised of only one of the first side wall member W1 and the second side wall member W2.

Also, a porous plastic filter F is located in the lower part (lower end) of the vertical passage P.

The fluid state identification device in this embodiment is held for the usage in a tank which will contain, for example, a urea aqueous solution, in a state that the device is suspended from above. As the measured fluid is poured into the tank, the fluid level goes up and eventually the device gets submerged in the measured fluid. At that time, the measured fluid is introduced into the cover 20 through the lower opening 9L and upper opening 9H made in the rear cover part 20R. How the measured fluid flows in the cover 20 is schematically shown by solid line arrows in FIGS. 12 and 13. The measured fluid which has flown into the rear area AR passes through the left area AS1 and the right area AS2 and reaches the front area AF.

Figure 10:
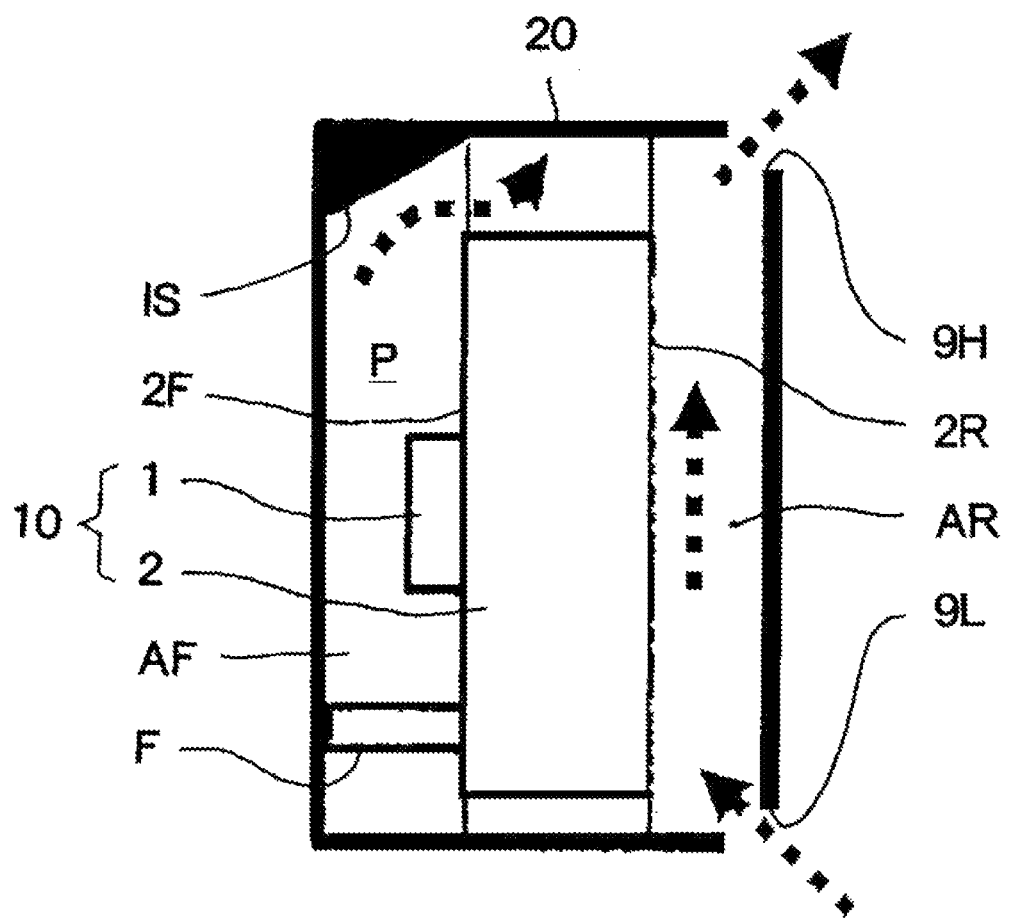
FIG. 10 is a schematic view for explaining the function of the fluid state identification device shown in FIG. 1.
Figure 11:
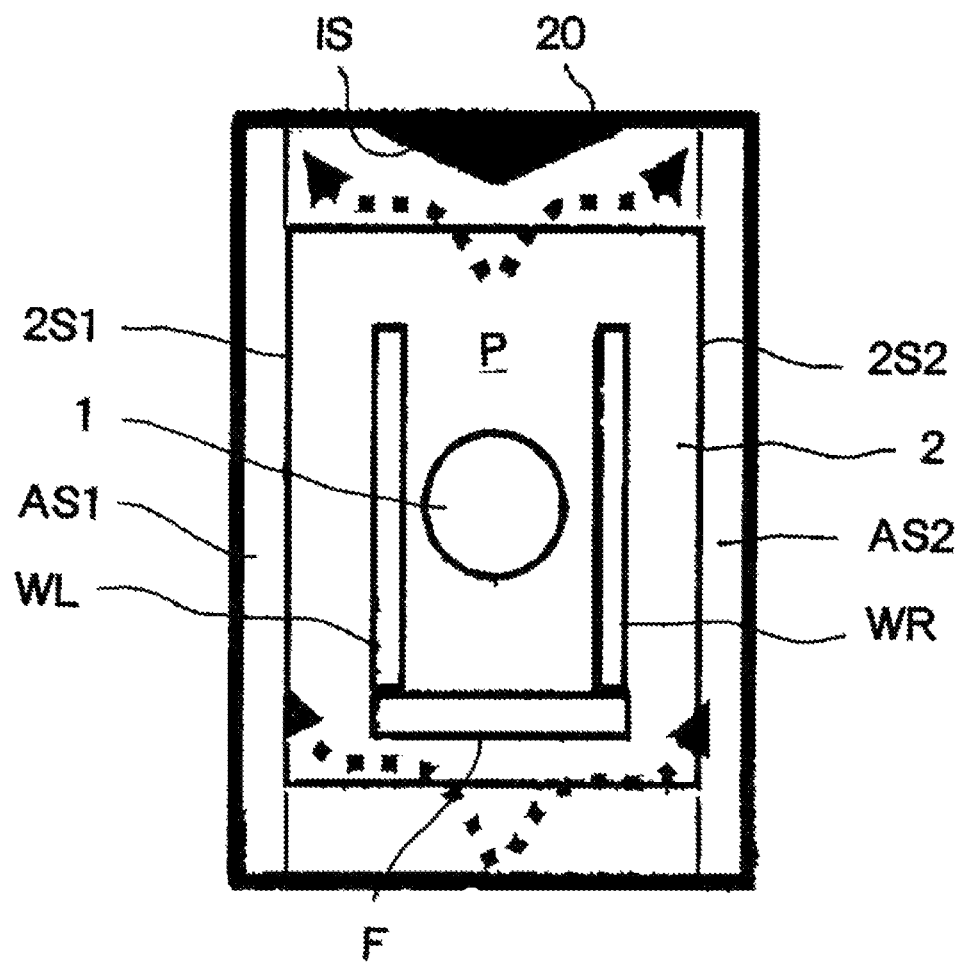
FIG. 11 is a schematic view for explaining the function of the fluid state identification device shown in FIG. 1.
Figure 12:
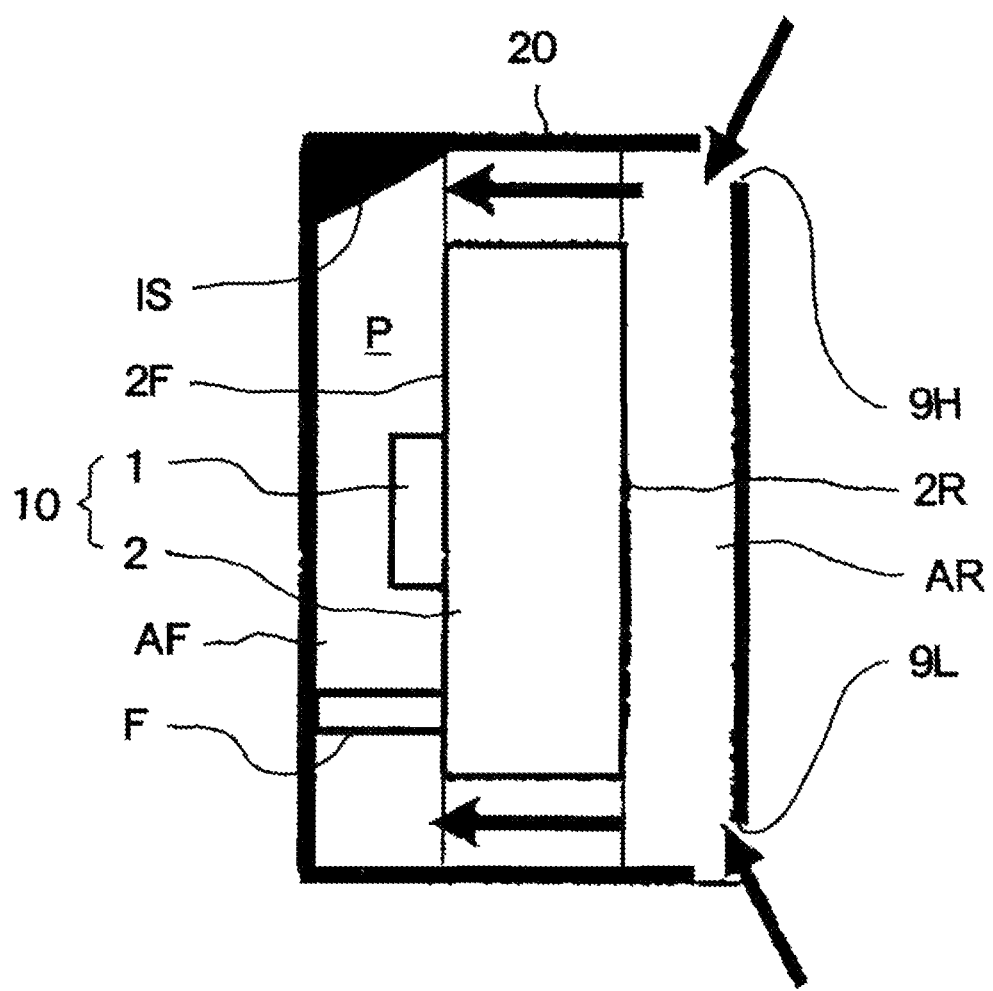
FIG. 12 is a schematic view for explaining the function of the fluid state identification device shown in FIG. 1.
Figure 13:
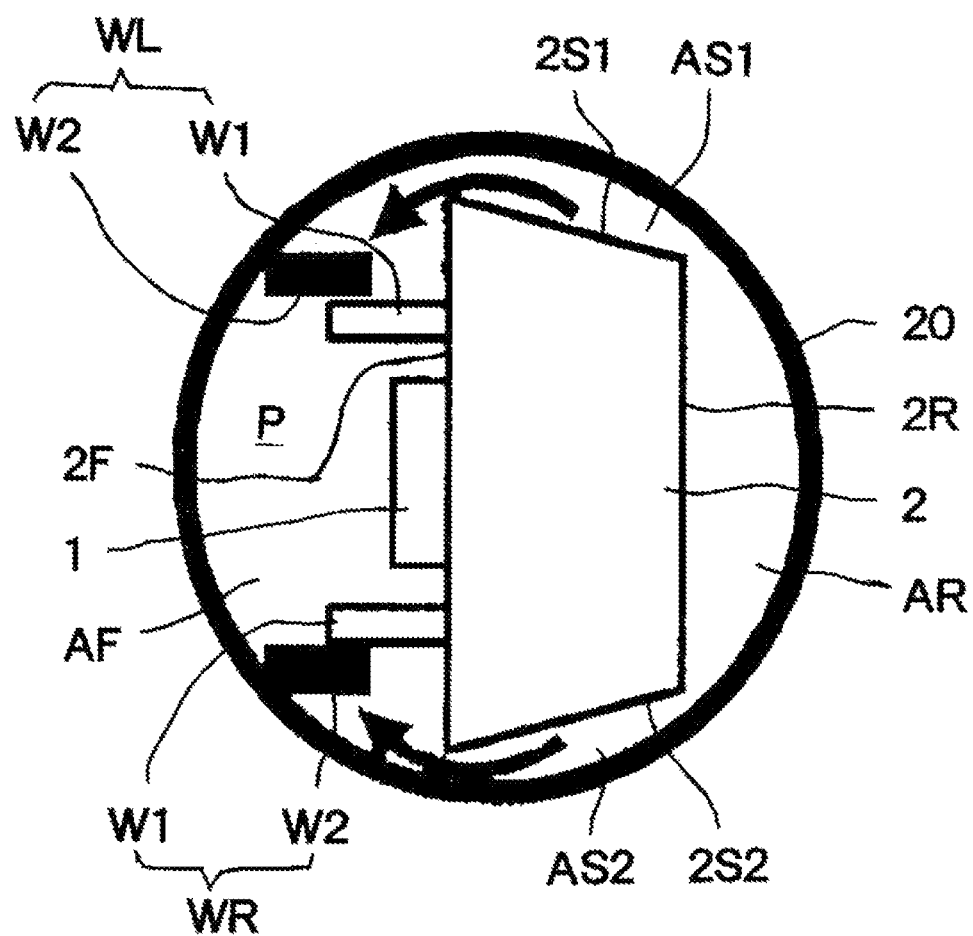
FIG. 13 is a schematic view for explaining the function of the fluid state identification device shown in FIG. 1.
Figure 14:
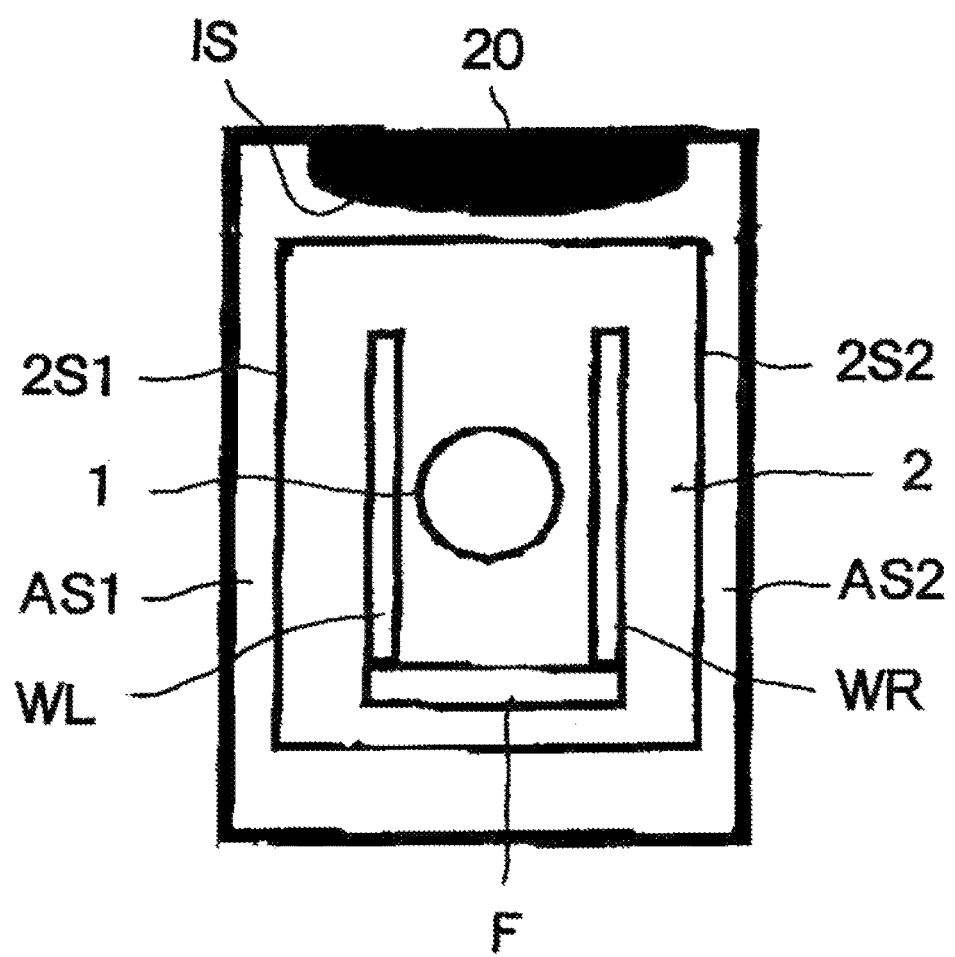
FIG. 14 is a schematic view showing a variation of the fluid state identification device shown in FIG. 1.

For various reasons, the measured fluid in the cover 20 may contain bubbles. One reason is that bubbles contained in the measured fluid outside the cover 20 are introduced through the lower opening 9L and upper opening 9H. In this case, as illustrated in FIG. 10, the bubbles introduced through the lower opening 9L mostly go up in the rear area AR and get out through the upper opening 9H. Even if bubbles reach under the front area AF, the bubbles are prevented by the filter F from getting into the vertical passage P and go up outside the vertical passage P and eventually get out through the upper opening 9H. The bubbles introduced through the upper opening 9H mostly get out through the upper opening 9H. Even if bubbles intrude to the front area AF, they stay in an upper part of the front area AF and are forced by the inclined surface IS of the top inner surface of the front cover part 20F to move upward in the leftward and rightward directions and/or the backward direction and eventually get out through the upper opening 9H. Alternatively the inclined surface IS may be a convex curved surface as illustrated in FIG. 14.

Another reason for the presence of bubbles in the measured fluid inside the cover 20 is that bubbles are generated in the measured fluid inside the cover 20 due to an external force such as vibration of the tank. In this case, bubbles in the rear area AR get out through the upper opening 9H as mentioned above. Bubbles in the lower part of the front area AF are prevented by the filter F from getting into the vertical passage P and go up outside the vertical passage P and eventually get out through the upper opening 9H. Bubbles in the upper part of the front area AF are forced by the inclined surface IS of the top inner surface of the front cover part 20F to move upward in the leftward and rightward directions and/or in the backward direction and eventually get out through the upper opening 9H.

Thus, in this embodiment, bubbles in the measured fluid less exert an unfavorable influence on the identification performance.

In addition, in this embodiment, since the sensor part 1 is located on the front surface part 2F of the support part 2 (namely opposite to the area adjacent to the rear surface part 2R of the support part 2 where the lower opening 9L and upper opening 9H of the cover 20 are located), forced flow of the measured fluid less exerts an unfavorable influence on the identification performance. Especially, since the vertical passage P using the left side wall WL and right side wall WR is located adjacent to the sensor part 1, the unfavorable influence of forced flow of the measured fluid on the identification performance is further reduced.

Figure 15:
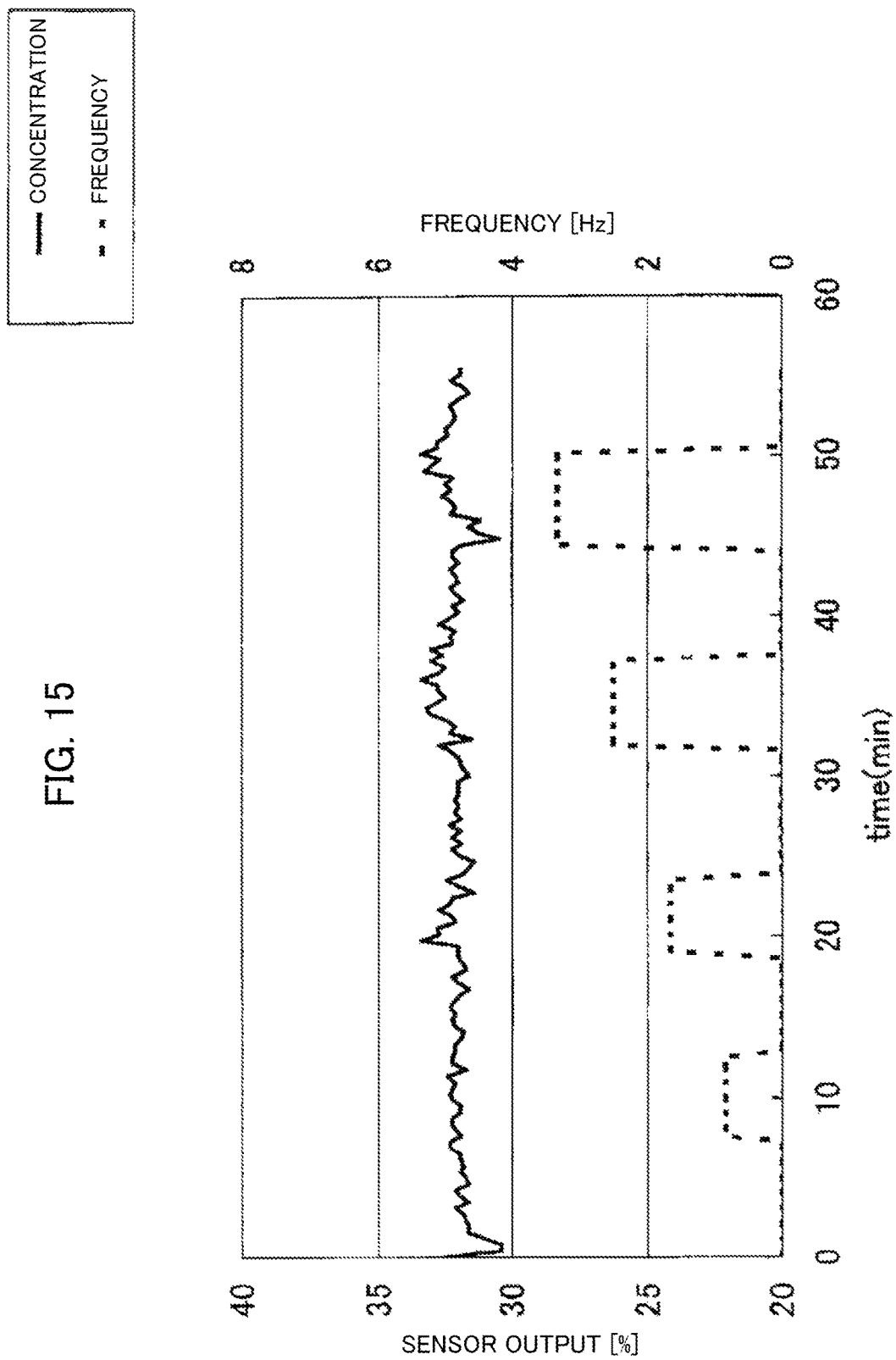
FIG. 15 is a graph showing sensor output obtained from a forced vibration test of a fluid state identification device according to the present invention.

FIG. 15 shows a graph of sensor output obtained in a forced vibration test of the fluid state identification device according to this embodiment. In this forced vibration test, a urea aqueous solution with a prescribed concentration which is contained in the urea aqueous solution tank was used as the measured fluid and vibration with an amplitude of 40 mm was applied to the tank at different frequencies of vibration to show change in the sensor output value (corresponding to the urea concentration in the urea aqueous solution). Even though the frequency of vibration was changed from 0 [Hz] to 3.3 [Hz], there was no significant change in sensor output.

Figure 16:
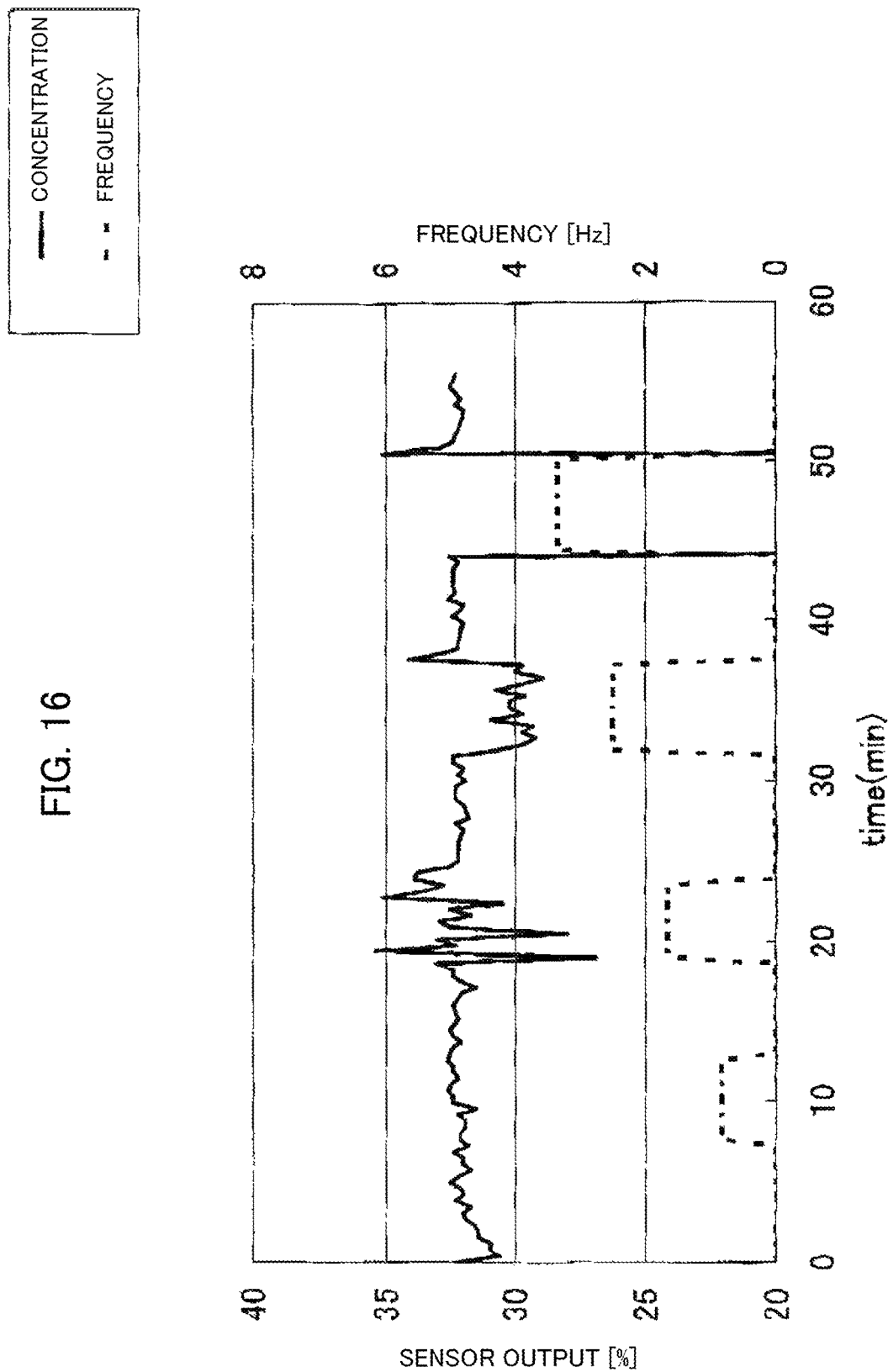
FIG. 16 is a graph showing sensor output obtained from a forced vibration test of a fluid state identification device for comparison with the fluid state identification device according to the present invention.

For comparison with the above fluid state identification device according to this embodiment, FIG. 16 shows a graph of sensor output obtained from a forced vibration test similar to the above test, using a fluid state identification device in which the lower opening and upper opening of the cover are located on the front surface part 2F of the support part 2. When the frequency of vibration was changed from 0 [Hz] to 3.3 [Hz], sensor output significantly fluctuated when the frequency of vibration was 1.7 [Hz] or more.

It is apparent from this that the present invention is advantageous in identification performance.

Figure 17:
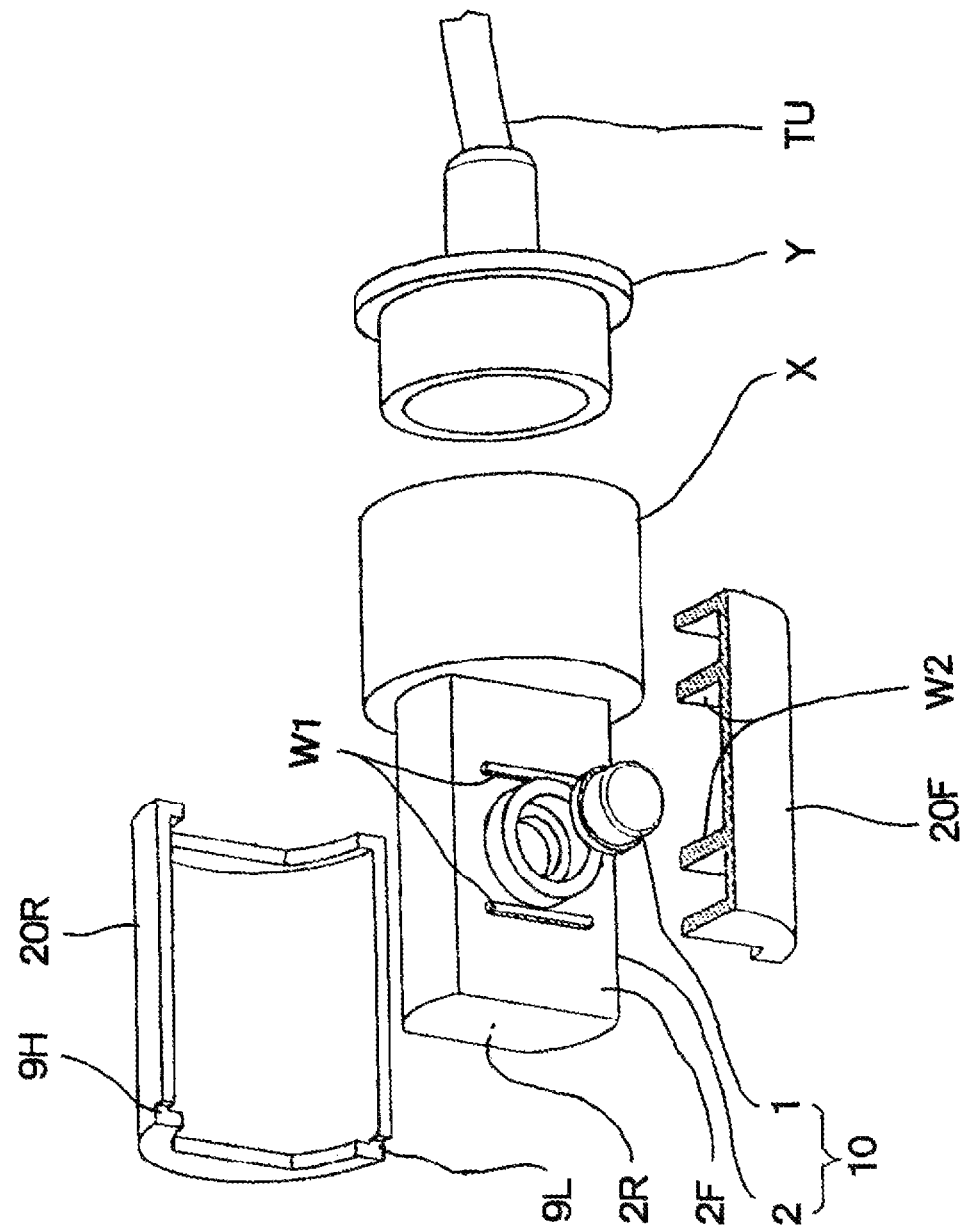
FIG. 17 is an exploded perspective view showing another embodiment of the fluid state identification device according to the present invention.
Figure 18:
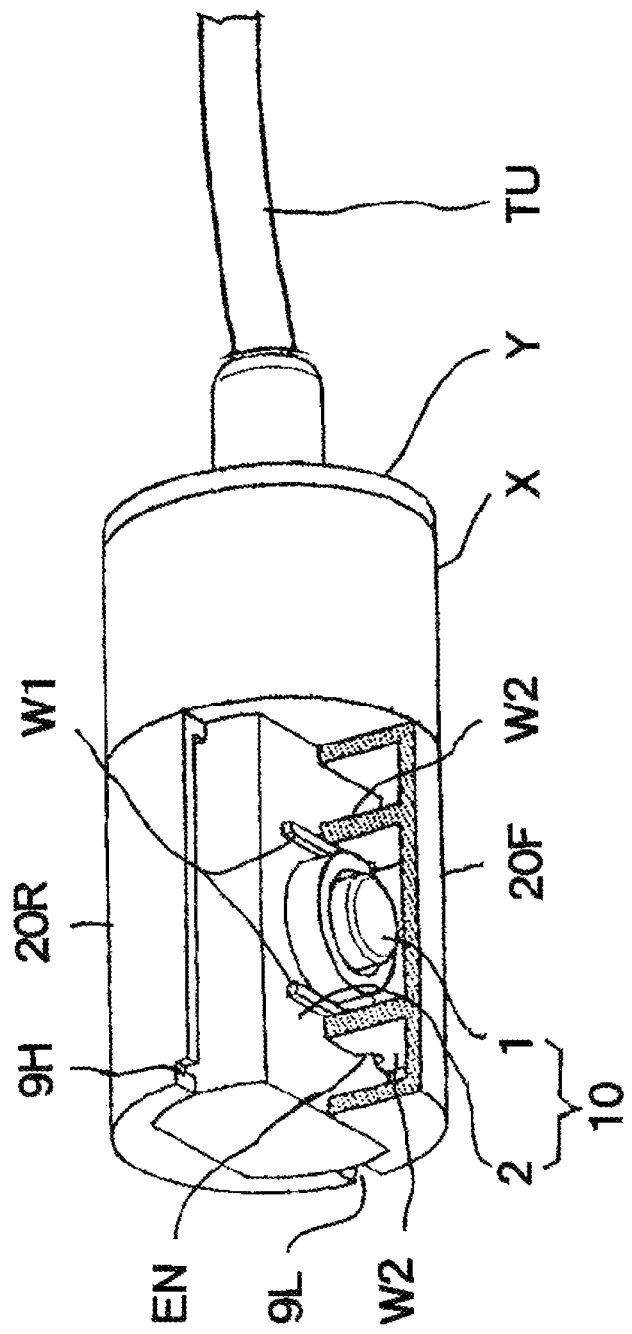
FIG. 18 is a partially cutaway perspective view of the fluid state identification device shown in FIG. 17.
Figure 19A:
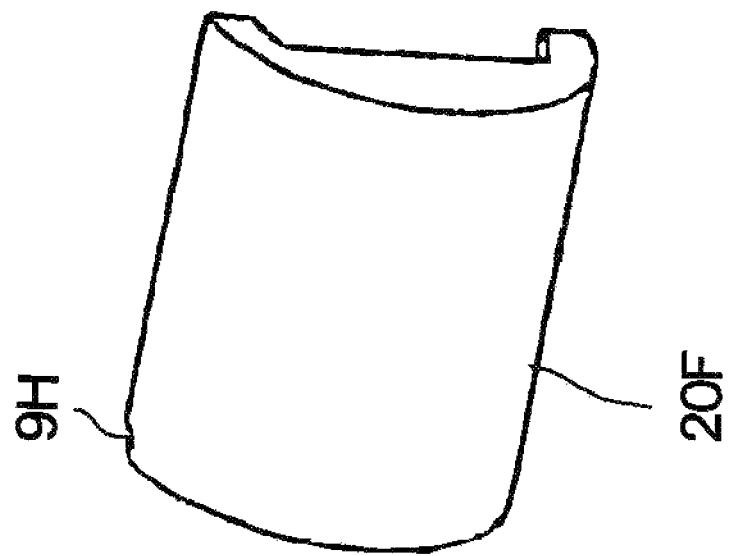
FIGS. 19A and 19B are perspective views of the front cover part of the fluid state identification device shown in FIG. 17.
Figure 19B:
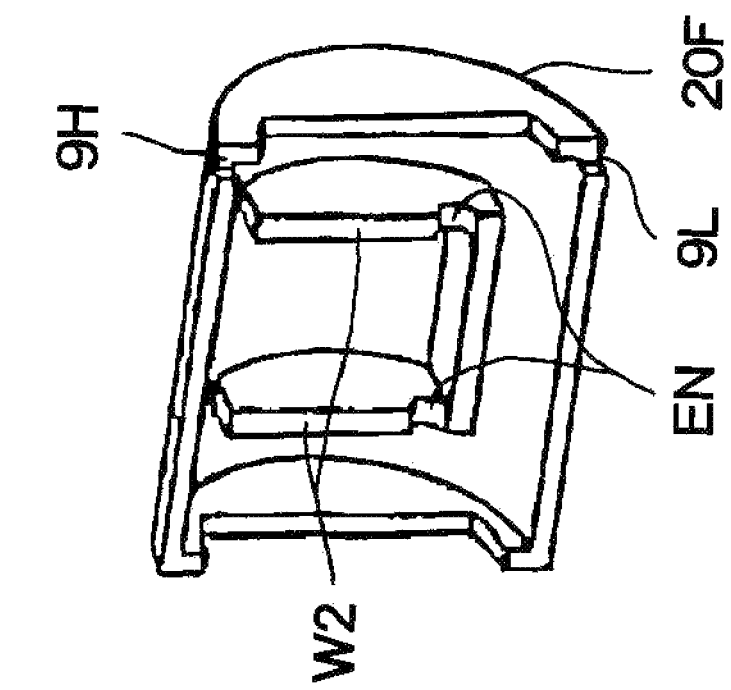
Figure 20B:
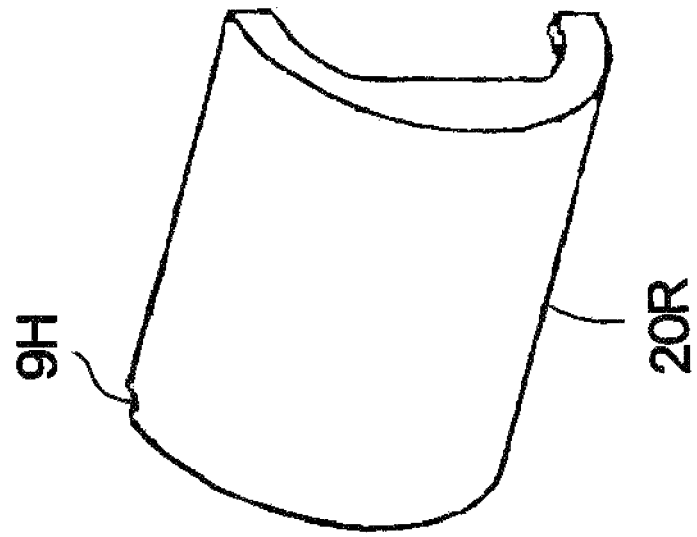
FIGS. 20A and 20B are perspective views of the rear cover part of the fluid state identification device shown in FIG. 17.
Figure 20A:
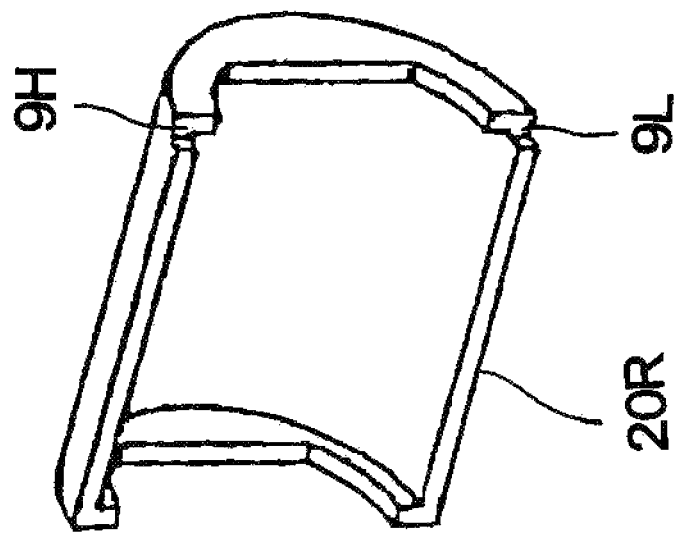
Figure 21:
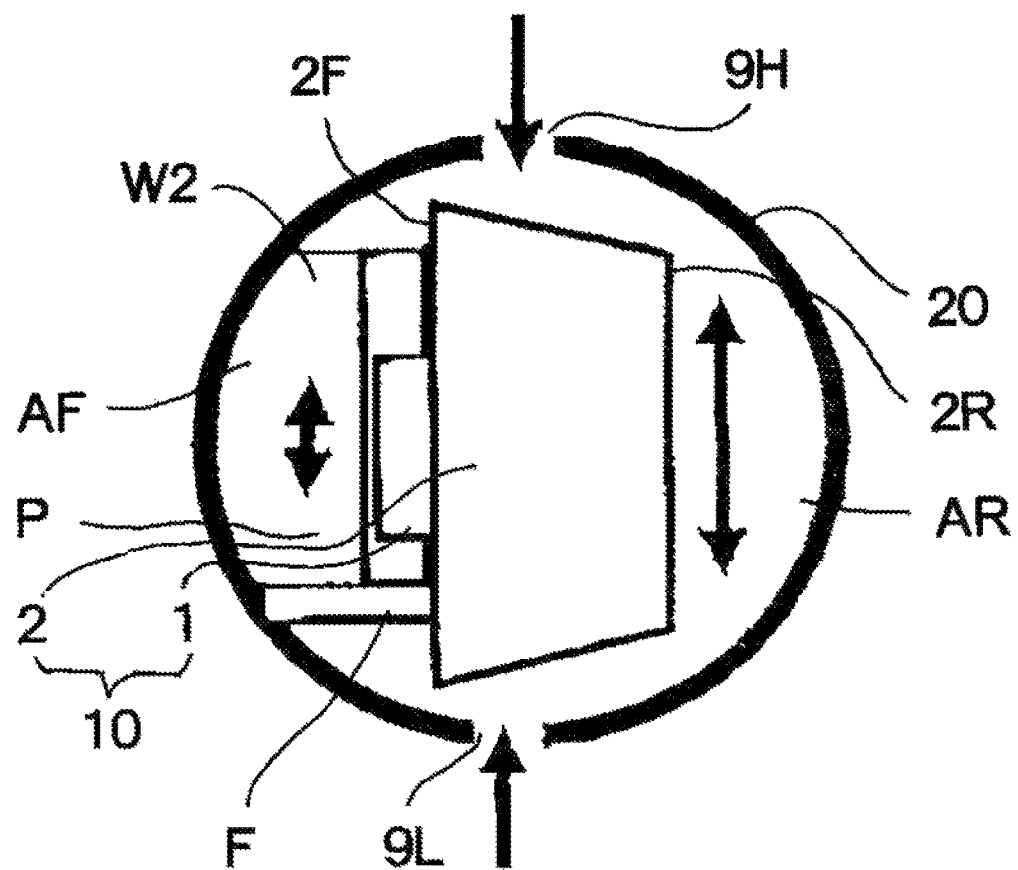
FIG. 21 is a schematic view for explaining the function of the fluid state identification device shown in FIG. 17.
Figure 22:
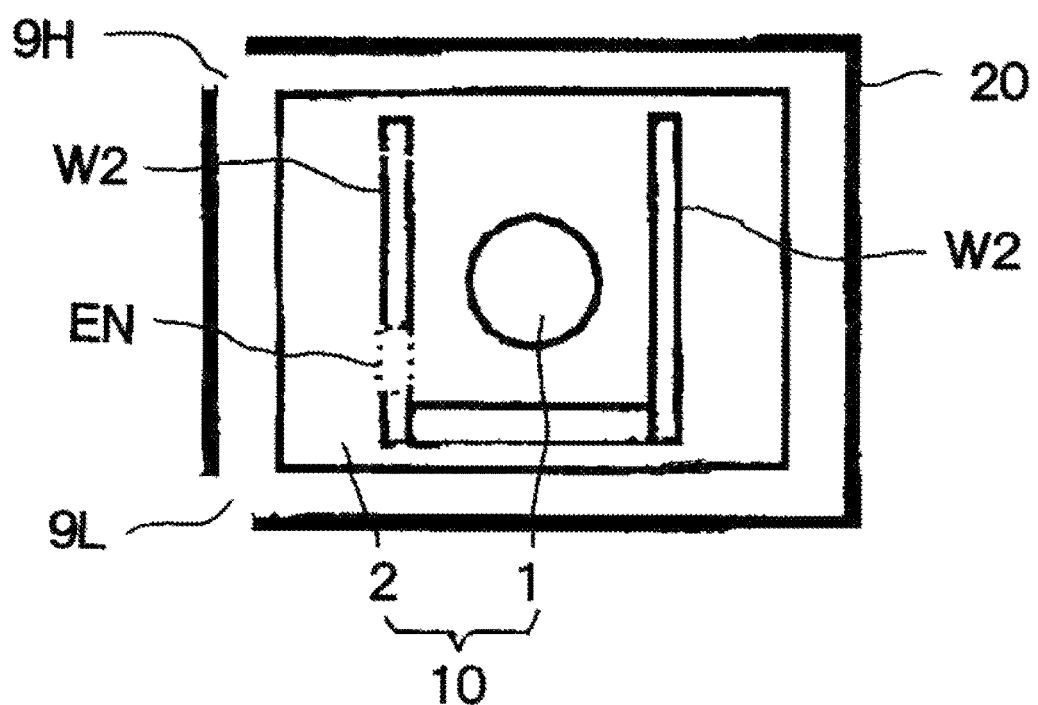
FIG. 22 is a schematic view of the fluid state identification device shown in FIG. 17.
Figure 23:
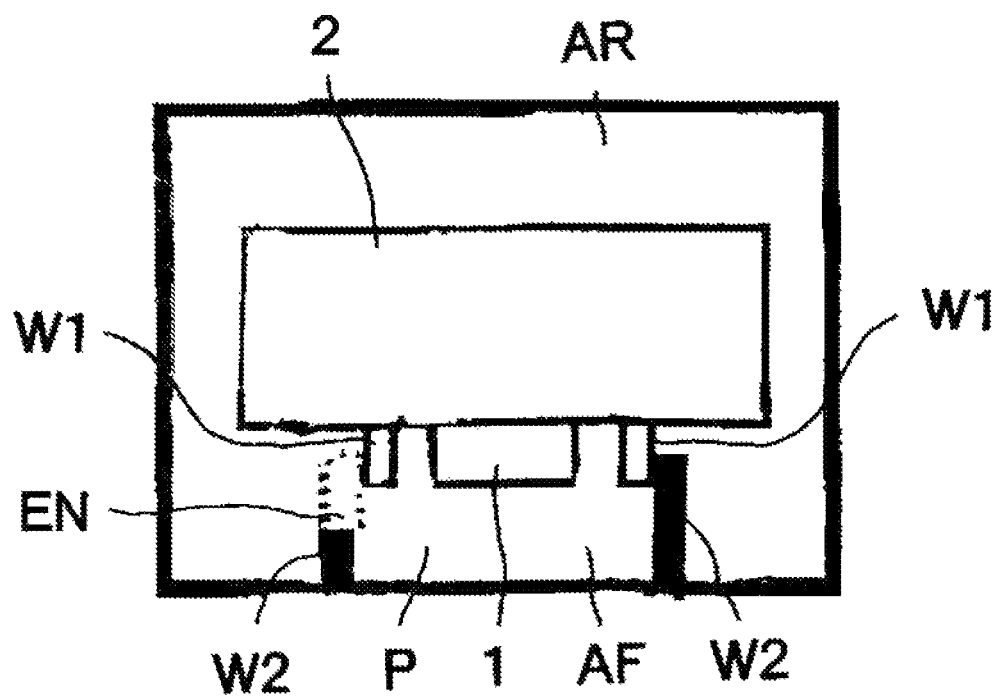
FIG. 23 is a schematic view of the fluid state identification device shown in FIG. 17.

FIG. 17 is an exploded perspective view showing another embodiment of a fluid state identification device according to the present invention; FIG. 18 is a partially cutaway perspective view of the fluid state identification device shown in FIG. 17; FIGS. 19A and 19B are perspective views of the front cover part of the fluid state identification device shown in FIG. 17; and FIGS. 20A and 20B are perspective views of the rear cover part of the fluid state identification device shown in FIG. 17. FIGS. 21 to 23 are all schematic views for explaining the function of the fluid state identification device shown in FIG. 17, in which FIG. 21 corresponds to a longitudinal cross section along the front-back direction, FIG. 22 corresponds to a longitudinal cross section along the left-right direction perpendicular to the front-back direction, and FIG. 23 corresponds to a transverse cross section along a horizontal plane. In these figures, members or parts with the same functions as those in FIGS. 1 to 14 are designated by the same reference signs.

In this embodiment, the same fluid state identification unit 10 as in the embodiment shown in FIGS. 1 to 14 is rotated 90 degrees from the position of the embodiment shown in FIGS. 1 to 14 to the horizontal direction when it is used.

The fluid state identification device in this embodiment is different from that in the embodiment shown in FIGS. 1 to 14, mainly in the structure of the cover 20.

Specifically, the lower opening 9L and upper opening 9H are formed at the left ends of the front cover part 20F and rear cover part 20R. As illustrated in FIG. 21, the longitudinal sectional shape of the support part 2 is asymmetric in the front-back direction (namely in the left-right direction in FIG. 21) and the front surface part 2F is larger than the rear surface part 2R in the vertical direction. Therefore, the lower opening 9L and upper opening 9H are located so that the minimum sectional area of the second fluid flow route running through the rear area AR is larger than the minimum sectional area of the first fluid flow route running through the front area AF.

Thus, regarding the fluidity inside the cover 20 of the fluid getting into and out of the cover 20 through the lower opening 9L and upper opening 9H, the fluidity in the second fluid flow route running through the rear area AR is higher than in the first fluid flow route running through the front area AF as schematically indicated by both the arrows in FIG. 21.

Furthermore, in this embodiment, an opening EN having an area smaller than the area of an upper opening of the vertical passage is formed in a lower part of the vertical passage P. The opening EN is made in the second side wall member W2. This further lowers the fluidity of the fluid in the vertical passage P. As illustrated in FIG. 19A, an opening EN may be formed in each of the left and right second side wall members W2 (in that case, the "area of the opening EN" should mean the sum of the actual areas of the two openings EN) or as illustrated in FIGS. 22 and 23, an opening EN may be formed in one of the second side wall members W2.

Thus, in this embodiment, as in the above embodiment shown in FIGS. 1 to 14, bubbles in the measured fluid less exert an unfavorable influence on the identification performance and in addition, forced flow of the measured fluid less exerts an unfavorable influence on the identification performance.

In the embodiments described so far, the sensor part includes a thermal sensor; however, the present invention may be applied to a device which uses a non-thermal sensor, for example, an ultrasonic sensor for the sensor part.

REFERENCE SIGNS LIST

1 . . . sensor part,
2 . . . support part
2F . . . front surface part
2R . . . rear surface part 2S1 . . . left side surface
2S2 . . . right side surface
9L . . . lower opening
9H . . . upper opening
10 . . . fluid identification unit
20 . . . cover
20F . . . front cover part
20R . . . rear cover part
X . . . housing main part
Y . . . housing cover part
TU . . . waterproof tube
AF . . . front area
AR . . . rear area
AS1 . . . left area
AS2 . . . right area
AL . . . lower part of the area
AH . . . upper part of the area
IS . . . inclined surface
P . . . vertical passage
WL . . . left side wall
WR . . . right side wall
W1 . . . first side wall member
W2 . . . second side wall member
F . . . porous plastic filter
EN . . . opening

The invention claimed is:

1. A fluid state identification device comprising a fluid state identification unit having a sensor part and a support part for supporting the sensor part and a cover surrounding the fluid state identification unit, wherein
in the fluid state identification unit, the support part has a front surface part and a rear surface part which are located opposite to each other and the sensor part is located on the front surface part side;
a lower opening for communicating a lower part of an area between the cover and the fluid state identification unit with an outside and an upper opening for communicating an upper part of the area between the cover and the fluid state identification unit with the outside are formed in the cover;
a first fluid flow route running through a front area adjacent to the front surface part of the support part from the lower opening to the upper opening and a second fluid flow route running through a rear area adjacent to the rear surface part of the support part from the lower opening to the upper opening are formed inside the cover;
the lower opening and the upper opening are located so that fluid fluidity in the second fluid flow route is higher than fluid fluidity in the first fluid flow route; and
both of the lower opening and the upper opening are located at a side of the rear area when seen from the support part.

2. The fluid state identification device according to claim 1, wherein the lower opening and the upper opening are located so that a minimum sectional area of the second fluid flow route is larger than a minimum sectional area of the first fluid flow route.

3. The fluid state identification device according to claim 2, wherein
a vertical passage adjacent to the sensor part is formed in the front area; and
the vertical passage is surrounded by a left side wall located left of the sensor part, a right side wall located right of the sensor part, the front surface part of the support part, and the cover and an upper part and a lower part thereof are open.

4. The fluid state identification device according to claim 2, wherein a top inner surface of the cover is an inclined surface.

5. The fluid state identification device according to claim 1, wherein a top inner surface of the cover is an inclined surface.

6. The fluid state identification device according to claim 1, wherein
a vertical passage adjacent to the sensor part is formed in the front area; and
the vertical passage is surrounded by a left side wall located left of the sensor part, a right side wall located right of the sensor part, the front surface part of the support part, and the cover and an upper part and a lower part thereof are open.

7. The fluid state identification device according to claim 1, wherein a top inner surface of the cover is an inclined surface.

8. A fluid state identification device comprising a fluid state identification unit having a sensor part and a support part for supporting the sensor part and a cover surrounding the fluid state identification unit, wherein
in the fluid state identification unit, the support part has a front surface part and a rear surface part which are located opposite to each other and the sensor part is located on the front surface part side;
a lower opening for communicating a lower part of an area between the cover and the fluid state identification unit with an outside and an upper opening for communicating an upper part of the area between the cover and the fluid state identification unit with the outside are formed in the cover;
a first fluid flow route running through a front area adjacent to the front surface part of the support part from the lower opening to the upper opening and a second fluid flow route running through a rear area adjacent to the rear surface part of the support part from the lower opening to the upper opening are formed inside the cover;
the lower opening and the upper opening are located so that fluid fluidity in the second fluid flow route is higher than fluid fluidity in the first fluid flow route;
a vertical passage adjacent to the sensor part is formed in the front area; and
the vertical passage is surrounded by a left side wall located left of the sensor part, a right side wall located right of the sensor part, the front surface part of the support part, and the cover and an upper part and a lower part thereof are open.

9. The fluid state identification device according to claim 8, wherein the left side wall and the right side wall are each comprised of a first side wall member protruding from the front surface part of the support part and/or a second side wall member protruding from an inner surface of the cover.

10. The fluid state identification device according to claim 9, wherein a porous filter is located in a lower part of the vertical passage.

11. The fluid state identification device according to claim 9, wherein an opening having an area smaller than an area of an upper opening of the vertical passage is formed in a lower part of the vertical passage.

12. The fluid state identification device according to claim 9, wherein a top inner surface of the cover is an inclined surface.

13. The fluid state identification device according to claim 8, wherein a porous filter is located in a lower part of the vertical passage.

14. The fluid state identification device according to claim 13, wherein an opening having an area smaller than an area of an upper opening of the vertical passage is formed in a lower part of the vertical passage.

15. The fluid state identification device according to claim 13, wherein a top inner surface of the cover is an inclined surface.

16. The fluid state identification device according to claim 8, wherein an opening having an area smaller than an area of an upper opening of the vertical passage is formed in a lower part of the vertical passage.

17. The fluid state identification device according to claim 16, wherein a top inner surface of the cover is an inclined surface.

18. The fluid state identification device according to claim 8, wherein a top inner surface of the cover is an inclined surface.

* * * * *